United States Patent
Murgida et al.

(10) Patent No.: US 6,231,259 B1
(45) Date of Patent: May 15, 2001

(54) VISCOUS PRODUCT DISPENSER WITH POROUS DOME

(75) Inventors: Matthew F. Murgida, Cambridge; William E. Tucker, Attleboro, both of MA (US)

(73) Assignee: The Gillette Company, Boston, MA (US)

(*) Notice: Subject to any disclaimer, the term of this patent is extended or adjusted under 35 U.S.C. 154(b) by 514 days.

(21) Appl. No.: 08/687,872

(22) Filed: Jul. 26, 1996

(51) Int. Cl.⁷ ........................................... B43K 5/06
(52) U.S. Cl. ......................... 401/175; 401/205; 401/206
(58) Field of Search .................................. 401/175, 205, 401/206

(56) References Cited

U.S. PATENT DOCUMENTS

| | | | |
|---|---|---|---|
| Re. 34,751 | 10/1994 | Thompson | 401/175 |
| 3,226,762 | 1/1966 | Norman | 401/175 |
| 3,616,970 | * 11/1971 | Baumann et al. | 401/175 X |
| 3,807,881 | 4/1974 | Seidler | 401/175 |
| 4,050,826 | 9/1977 | Berghahn | 401/196 |
| 4,111,567 | * 9/1978 | Berghahn et al. | 401/205 X |
| 4,139,127 | 2/1979 | Gentile | 401/175 |
| 4,480,940 | 11/1984 | Woodruff | 401/206 |
| 5,018,894 | 5/1991 | Goncalves | 401/202 |
| 5,073,057 | 12/1991 | Lathrop | 401/206 |
| 5,122,158 | 6/1992 | Kuroda | 401/202 |
| 5,131,777 | 7/1992 | Junji | 401/202 |
| 5,230,579 | 7/1993 | Klawson | 401/205 |
| 5,547,302 | 8/1996 | Dornbusch | 401/175 |
| 5,567,073 | 10/1996 | de Laforcade | 401/202 |

FOREIGN PATENT DOCUMENTS

| | | | |
|---|---|---|---|
| 249473 | * 10/1962 | (AU) | 401/175 |
| 732273 | 9/1996 | (EP) . | |
| 2240032 | * 7/1991 | (GB) | 401/205 |

* cited by examiner

Primary Examiner—David J. Walczak
(74) Attorney, Agent, or Firm—Stephan P. Williams

(57) ABSTRACT

The present invention is directed to a composition comprising an antiperspirant salt suspended in a carrier vehicle thickened with a silicone latex. The composition typically comprises about 50 to 90% carrier vehicle, which is advantageously substantially comprised of a volatile silicone, about 3 to 30% antiperspirant salt, which is typically an aluminum chlorohydrate or aluminum-zirconium chlorohydrate, and about 3–25% silicone latex. Preferably the composition will contain an auxiliary thickening agent such as a fumed silica, typically in an amount of 0.01 to 0.1%. The composition will preferably have a viscosity of about 12,000 to 50,000 cP. The present invention also embraces an apparatus for delivering the above-described composition, said apparatus having a porous dome with a porosity of about $150\mu$ to $400\mu$ through which the composition is delivered.

17 Claims, 1 Drawing Sheet

VISCOUS PRODUCT DISPENSER WITH POROUS DOME

BACKGROUND OF THE INVENTION

This invention relates to antiperspirant and deodorant compositions which contain a silicone latex as a thickening agent. In particular it relates to such compositions which additionally contain an auxiliary thickening agent.

Silicone latex thickened solvents and cosmetic compositions containing such silicone latex thickened solvents are described in U.S. Ser. No. 08/596,853 filed on Feb. 5, 1996. The silicone latex is a high internal phase dispersion of crosslinked silicone rubber particles in water. When added to a solvent such as cyclomethicone, it swells and substantially increases the viscosity of the solvent.

SUMMARY OF THE INVENTION

The present invention is directed to a composition comprising an antiperspirant salt suspended in a carrier vehicle thickened with a silicone latex. The composition typically comprises about 50 to 90% carrier vehicle, which is advantageously substantially comprised of a volatile silicone, about 3 to 30% antiperspirant salt, which is typically an aluminum chlorohydrate or aluminum-zirconium chlorohydrate, and about 3–25% silicone latex. Preferably the composition will contain an auxiliary thickening agent such as a fumed silica, typically in an amount of 0.01 to 0.1%. The composition will preferably have a viscosity of about 12,000 to 50,000 cP. The present invention also embraces an apparatus for delivering the above-described composition, said apparatus having a porous dome with a porosity of about $150\mu$ to $400\mu$ through which the composition is delivered.

DETAILED DESCRIPTION OF THE INVENTION

Figure 1:
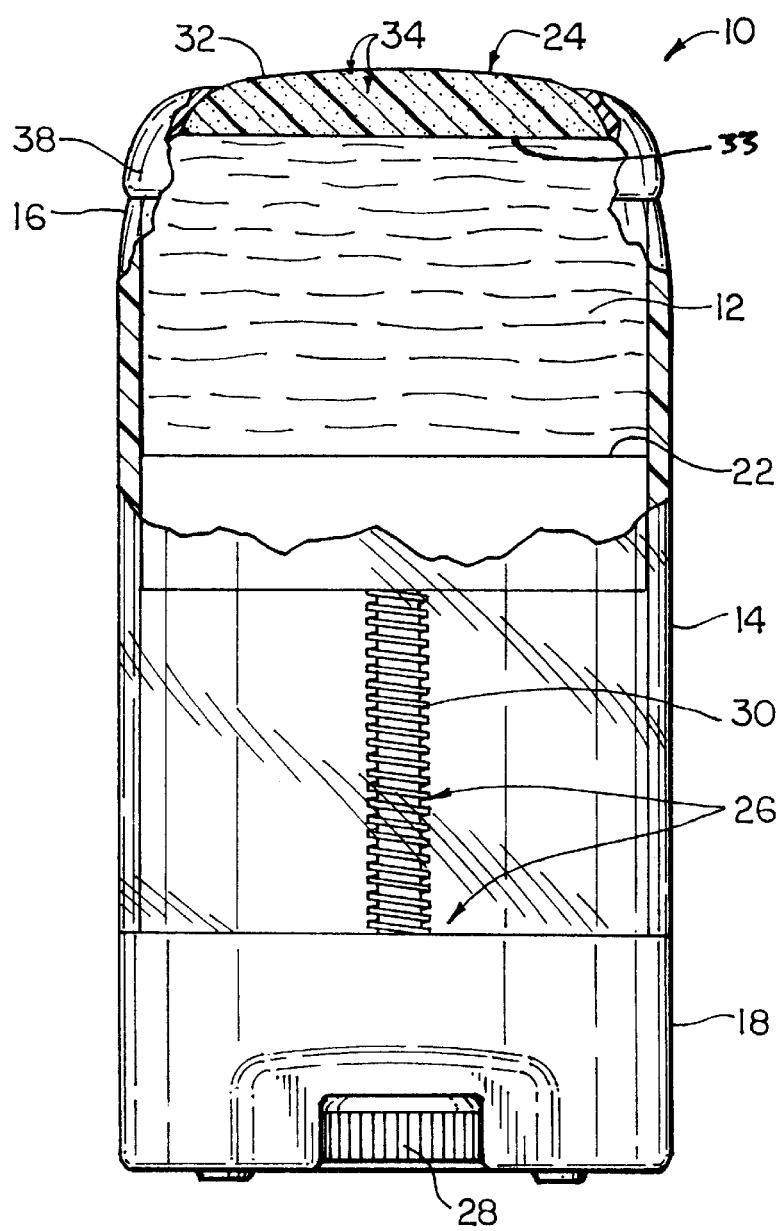
FIG. 1 is a front elevational view, shown in partial cross section, of a dispenser for an antiperspirant or deodorant composition of the present invention.

The antiperspirant and deodorant compositions of the present invention will include as the main vehicle a silicone latex thickened organic and/or silicone compound.

The silicone latex is a high internal phase dispersion of crosslinked silicone rubber particles in water. The silicone latex is described in U.S. Ser. No. 08/596,853 filed on Feb. 5, 1996, the contents of which are incorporated herein by reference. The silicone latex is formed by emulsifying 100 parts of siloxane polymer with 0.5 to 10 parts surfactant, such as Isolaureth-6, and 0.5 to 25 parts water, adding catalyst and crosslinker or self-catalytic crosslinker, and curing to form a dispersion of the silicone rubber particles in water. Preferably the silicone latex has a high solids content of at least 90% crosslinked silicone rubber particles.

A preferred silicone latex is available from Dow Corning as DC-3-2380. For easier handling, it is also available as DC-3-2390, which is a mixture of about 5 to 15%, typically about 11%, of the silicone latex in cyclomethicone (DC 344). When used in this form, it should be added in an amount which gives the desired quantity of silicone latex in the final composition. This silicone latex is the hydrosilation reaction product of a vinyl functional siloxane polymer and a hydride functional siloxane polymer prepared in emulsion, wherein the vinyl functional siloxane polymer is represented by the formula $CH_2=CH-((CH_3)_2SiO)_xCH=CH_2$ in which x is an integer such that the viscosity of the polymer is between 5000 and 20,000 cP, and wherein the hydride functional siloxane polymer is represented by the formula $(CH_3)_3SiO((CH_3)_2SiO)_y(CH_3HSiO)_zSi(CH_3)_3$ in which y is an integer between 3 and 20 and z is an integer greater than 3 and less than 10.

The amount of silicone latex to be incorporated into the composition may be varied depending upon the thickening or viscosity desired in the final composition, which may range from a thick liquid to a cream or gel consistency up to a paste or soft-solid. Generally, the silicone latex will be utilized in an amount of about 3 to 25% by weight of the composition, preferably about 5 to 20%. Most preferably, the amount of silicone latex will comprise about 6 to 12% by weight of the composition.

The main portion of the carrier vehicle will be an organic or silicone compound or mixtures thereof. Preferably, the vehicle will be comprised substantially of a volatile silicone. Volatile silicones are well-known in the art and may be linear or cyclic. They have a boiling point under 250° C. and a viscosity less than 10 cP. Preferred are the cyclomethicones such as DC 244, DC 245, DC 344 and DC 345. The volatile silicones give the composition a dry feel and leave substantially no residue.

While volatile silicones are preferred, other silicones and/or organic compounds may be utilized in the carrier vehicle, particularly when included in addition to the volatile silicones to improve application aesthetics. These include non-volatile silicones such as dimethicone and dimethicone copolyol and aliphatic hydrocarbons such as mineral oil and hydrogenated polyisobutene. Of course, a variety of well-known emollients such as diisopropyl adipate, diisopropyl sebacate, PPG-5-Ceteth-20, Octy Isononanoate, and PPG-14 Butyl Ether may be included in the vehicle to improve application aesthetics. Generally, the vehicle will comprise about 50 to 90% of the composition by weight, preferaby about 65 to 85%.

Antiperspirant salts which may be used in the compositions of the present invention include any of the conventional aluminum, zirconium and aluminum-zirconium salts known to be useful in antiperspirant compositions. These salts include aluminum halides and aluminum hydroxy halides (e.g., aluminum chlorohydrate), and mixtures or complexes thereof with zirconyl oxyhalides and zirconyl hydroxyhalides (e.g. aluminum-zirconium chlorohydrate). It has been surprisingly found that addition of the antiperspirant salt to a silicone latex thickened carrier vehicle substantially further increases the viscosity of the composition, thus making it possible to readily achieve a more viscous composition, especially one with a creamy type consistency.

Preferred aluminum salts are those having the general formula $Al_2(OH)_{6-a}X_a$ wherein X is Cl, Br, I or $NO_3$, and a is about 0.3 to about 4, preferably about 1 to 2, such that the Al to X mole ratio is about 1:1 to 2.1:1. These salts generally have some water of hydration associated with them, typically on the order of 1 to 6 moles per mole of salt. Most preferably, the aluminum salt is aluminum chlorohydrate (i.e. X is Cl) and a is about 1, such that the aluminum to chlorine mole ratio is about 1.9:1 to 2.1:1.

Preferred aluminum-zirconium salts are mixtures or complexes of the above-described aluminum salts with zirconium salts of the formula $ZrO(OH)_{2-pb}Y_b$ wherein Y is Cl, Br, I, $NO_3$, or $SO_4$, b is about 0.8 to 2, and p is the valence of Y. The zirconium salts also generally have some water of hydration associated with them, typically on the order of 1 to 7 moles per mole of salt. Preferably the zirconium salt is zirconyl hydroxychloride of the formula $ZrO(OH)_{2-b}Cl_b$, wherein b is about 1 to 2, preferably about 1.2 to about 1.9. The preferred aluminum-zirconium salts have an Al:Zr ratio of about 1.7 to about 12.5, most preferably about 2 to about 10, and a metal:X+Y ratio of about 0.73 to about 2.1, preferably about 0.9 to 1.5. A preferred salt is aluminum-zirconium chlorohydrate (i.e. X and Y are Cl), which has an Al:Zr ratio of about 2 to about 10 and a metal:Cl ratio of about 0.9 to about 2.1. Thus, the term aluminum-zirconium chlorohydrate is intended to include the tri-, tetra-, penta- and octa-chlorohydrate forms. The aluminum-zirconium salt complexes may also contain a neutral amino acid, preferably glycine, typically with a Gly:Zr ratio of about 1:1 to 4:1.

It is especially preferred to utilize enhanced efficacy aluminum and aluminum-zirconium antiperspirant salts in the compositions of the present invention. By "enhanced efficacy antiperspirant salts" is meant antiperspirant salts which, when reconstituted as 10% aqueous solutions, produce an HPLC chromatogram (as described, for example, in U.S. Pat. No. 5,330,751, which is incorporated herein by reference) wherein at least 70%, preferably at least 80%, of the aluminum is contained in two successive peaks, conveniently labeled peaks 3 and 4, wherein the ratio of the area under peak 4 to the area under peak 3 is at least 0.5, preferably at least 0.7, and most preferably at least 0.9 or higher. Any suitable HPLC technique may be employed provided that it is capable of resolving the Al component into five peaks. The enhanced efficacy (or activated) antiperspirant salts are well-known in the industry and are commercially available from several suppliers.

Sufficient antiperspirant salt should be added so that the final composition, after all components are added, includes between about 3% and about 30%, preferably about 6% to 25%, of the antiperspirant salt by weight. Generally, the composition will be designated an antiperspirant composition if it contains sufficient antiperspirant salt to effectively inhibit perspiration. This amount of antiperspirant salt will typically be greater than about 10% by weight. Below that amount, the composition will generally be designated a deodorant composition. It should be noted that reference throughout this application to weight percent of antiperspirant salt is intended to be calculated in accordance with the standard industry method, which includes bound water and glycine. If the amount of antiperspirant salt is calculated in accordance with the new U.S.P. method, which excludes bound water and glycine, the range of weight percent will be somewhat lower. It is especially preferred to utilize a particulate antiperspirant salt with a relatively small particle size, preferably in the range of about 1 to $50\mu$, to achieve the best suspension and aesthetic characteristics. Most preferred are ultrafine antiperspirant salts wherein at least 90% of the particles are under $11\mu$.

While the compositions of the present invention may be formulated and used with only the above-described basic constituents, it is also desirable to add other optional components to achieve desired application aesthetics or other effects. For example, the addition of auxiliary thickening agents has been found to substantially improve the application aesthetics by thickening or increasing the viscosity of the composition to desired levels while maintaining the amount of the silicone latex at relatively low levels. It has been found that high levels of the silicone latex, while effective at thickening the composition, tend to diminish the application aesthetics, for example by giving a too greasy and/or too sticky feel. The addition of an auxiliary thickening agent, especially the preferred silicas, give the composition a drier, less sticky feel.

Any conventional thickening agents known for use in antiperspirant and deodorant compositions may be utilized, alone or in combination, as an auxiliary thickening agent in the compositions of the present invention. These include waxes, fatty acids, fatty alcohols, fatty amides, clays, silicas, starches, silicate powders, particulate polyolefins (e.g. polyethylene), etc.

Particularly advantageous as auxiliary thickening agents are the silicas, preferably fumed silicas, which have been found to substantially increase the viscosity of the composition at very low levels. Generally, the silica will be added in an amount of less than 1%, preferably less that 0.5%, and more preferably less than 0.1%. It has been surprisingly found that an amount as low as 0.01% to 0.02% fumed silica will substantially increase the viscosity of the composition, particularly when the composition contains higher levels (i.e. >12%) of antiperspirant salt. Especially preferred silicas are Aerosil 200 and Aerosil 300, available from Degussa Corporation.

The composition may contain an antimicrobial or deodorant active agent such as triclosan or hyamine. These agents are typically included in an amount of about 0.1 to about 3% by weight of the composition. The composition may also contain a fragrance, which is typically included in an amount of less than 2.5%, preferably less than about 1.5%, of the composition by weight.

The viscosity of the composition may be adjusted to any desired level by adjusting the amount of silicone latex along with any auxiliary thickening agent present. It has been found that a composition with especially desirable application aesthetics will have a viscosity of about 12,000 to 50,000 cP, preferably about 18,000 to 30,000 cP. It has been found that such a composition may advantageously be delivered through an applicator with a porous dome having an average pore size of about 150 to 400 $\mu$m, preferably about 250 $\mu$m. Such a porous dome is made from polyolefin particles such as low density polyethylene particles (preferably spherical particles) which have been sintered or fused together into a rigid, non-deformable dome shape. Such porous domes are available from Porex Technologies and Interflo Technologies.

While porous domes have been previously used to deliver liquid compositions (see, for example U.S. Pat. Nos. 4,050, 826 and 5,230,579), it is not believed that anyone considered it possible or desirable to deliver a viscous or cream-like composition through such a dome. This may be due to the fact that the domes previously used had a much lower porosity and could not effectively deliver a viscous or cream-like composition as contemplated by the present invention. However, the combination of a composition with a viscosity of 12,000 to 50,000 cP, preferably 18,000 to 30,000 cP, a; with a porous dome of 150 to 400 $\mu$m preferably about 250$\mu$m porosity has been found to provide excellent application aesthetics and is considered highly desirable to the consumer.

Figure 2:
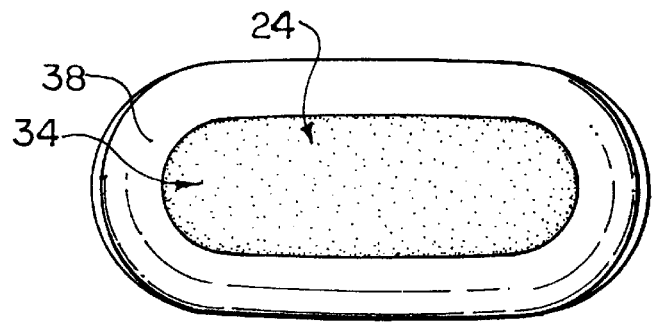
FIG. 2 is a top plan view of the dispenser of FIG. 1, which illustrates the porous dome through which the antiperspirant or deodorant composition is dispensed.

Referring now to FIGS. 1 and 2, there is illustrated an apparatus 10 for dispensing a cream or thin paste 12 having a viscosity of 12,000 to 50,000 cP, preferably 18,000 to 30,000 cP, the apparatus being comprised of a container 14 having a top end 16 and a bottom end 18 and a container opening being defined between the top end and the bottom end. The container 14 is filled with a cream or thin paste 12 within the container reservoir, which is that portion of the container opening between the platform 22 and the porous dome 24.

A transport mechanism 26 is operatively engaged to the bottom end 18 of the container, the transport mechanism capable of transporting the cream 12 toward the top end 16 of the container 14. The transport mechanism 26 will typically include a turn buckle 28 coupled to a threaded shaft 30 which threadedly engages the platform 22, as is well known to the art. Rotary motion of the turn buckle 28 causes the platform to advance upwardly on threaded shaft 30. This upward movement of the platform forces the cream 12 upwardly towards the porous dome 24.

The porous dome 24 is operatively engaged to the top end 16 of the container and is formed across a substantial portion of the top end. The porous dome has an externally disposed upper surface 32 and an internally disposed bottom surface 33, which, during use, is in contact with the cream or paste over a major portion of said bottom surface. The porous dome 24 is made from a sintered low density polyethylene and has interconnected pores 34 defined therethrough which give it a porosity of about 150 to 400 $\mu$m, preferably about 250 $\mu$m. The porous dome 24 is operatively engaged to the container 14 such as by use of a support skirt 38 which is operatively engaged to the top end of the container 14.

In operation, the transport mechanism 26 forces the cream or thin paste 12 to flow from the container opening through the pores of the porous dome 24 to the upper surface 32. The porous dome is typically shaped to engage with portions of the human body such as the underarm and is, therefore, typically formed to have a smooth rounded contoured shape to ease application of the cream or thin paste to the skin.

The invention may be further described by the following examples which are for illustrative purposes only.

| Ingredient | Weight Percent | | | | |
|---|---|---|---|---|---|
| | Ex. 1 | Ex. 2 | Ex. 3 | Ex. 4 | Ex. 5 |
| Silicone latex [1] | 6.00 | 6.00 | 6.00 | 6.30 | 6.30 |
| Cyclomethicone [2] | 70.35 | 68.85 | 68.94 | 68.64 | 68.34 |
| Al—Zr tetrachlorohydrate-gly | 23.50 | 23.50 | 23.50 | 23.50 | 23.50 |
| Dimethicone copolyol [3] | | | 0.75 | 0.75 | 0.75 |
| Diisopropyl adipate | | 1.00 | 0.60 | 0.60 | 0.60 |
| Silicone wax [4] | | 0.50 | | | |
| Silica [5] | | | 0.01 | 0.01 | 0.01 |
| Fragrance | 0.15 | 0.15 | 0.20 | 0.20 | 0.20 |

Examples 6 to 10 - Deodorant

| Ingredient | Weight Percent | | | | |
|---|---|---|---|---|---|
| | Ex. 6 | Ex. 7 | Ex. 8 | Ex. 9 | Ex. 10 |
| Silicone latex [1] | 6.50 | 6.50 | 7.20 | 7.20 | 6.50 |
| Cyclomethicone [2] | 81.15 | 87.60 | 73.50 | 76.80 | 82.50 |
| Al—Zr tetrachlorohydrate-gly | 8.00 | 4.50 | 8.00 | 6.00 | 7.00 |
| Dimethicone copolyol [3] | | | | | 0.80 |
| Diisopropyl adipate | 3.00 | | 3.00 | 3.00 | 2.00 |
| Silica [5] | 0.35 | 0.35 | | | 0.20 |
| Fragrance | 1.00 | 0.75 | 1.00 | 1.00 | 1.00 |
| Triclosan | | 0.30 | 0.30 | 3.00 | |
| Zinc oxide | | | 7.00 | | |
| Al starch octenyl succinate [6] | | | | 3.00 | |

The above-described compositions were made in the following manner. All of the ingredients except for the Al-Zr salt, silica, fragrance, zinc oxide (if present) and starch (if present) are combined in a closed mixing vessel equipped with a dual 3-blade impeller and mixed until uniform. The silica (if present) is added, mixed until uniform, and the mixture is passed through a Sonolator shear device (Sonic Corp., Model A running at 500 psi through a 0.004 in. diameter orifice) to increase the viscosity, then flowed into another closed mixing vessel equipped with both a side scraping agitator and a central impeller. The Al—Zr salt is added and mixed until uniform, then the zinc oxide (if present) or starch (if present) is added. This addition further increases the viscosity. The fragrance is then added and mixed until uniform.

While particular embodiments of the invention have been shown and described for illustrative purposes, it will be apparent to those skilled in the art that various changes and modifications may be made without departing from the spirit and scope of the invention, which is defined by the claims which follow.

What is claimed is:

1. Apparatus for dispensing an antiperspirant or deodorant composition having a viscosity of about 12,000 to 50,000 cP, said apparatus comprising:

a container having a top end and a bottom end and a container opening defined therebetween, said container opening at least partially filled with said composition, a transport mechanism operatively engaged to said bottom end for transporting at least a portion of said composition toward said top end, and a rigid, non-deformable, sintered polyolefin porous dome operatively engaged to said top end and formed across a substantial portion of said top end, said porous dome having an externally disposed upper surface with a smooth rounded contoured shape to engage an underarm portion of a human body and an internally disposed bottom surface which, during use, is in contact with said composition over a major portion of said bottom surface, said porous dome having interconnected pores therethrough to provide an average porosity of about 150 $\mu$m to about 400 $\mu$m, operation of said transport mechanism forcing said composition to flow from said container opening through said pores to said upper surface.

2. Apparatus for dispensing a viscous antiperspirant or deodorant composition having a viscosity of about 12,000 to 50,000 cP to an underarm portion of a human body, said apparatus comprising a container which defines a reservoir that is at least partially filled with said viscous composition, and an applicator head having interconnected pores affixed at one end of said container, wherein said applicator head comprises a rigid, non-deformable, sintered porous polyolefin with an externally disposed upper surface and an internally disposed bottom surface which, during use, is in contact with said viscous composition over a major portion of said bottom surface, said apparatus further comprising a transport mechanism to force said viscous composition from said reservoir through the pores of said applicator head for distribution of said viscous composition onto said upper surface.

3. The apparatus of claim 2 wherein said applicator head has an average porosity of about 150 to 400 $\mu$m.

4. The apparatus of claim 2 wherein said applicator head comprises a sintered porous polyethylene.

5. The apparatus of claim 4, wherein said applicator head has an average porosity of about 150 to 400 $\mu$m.

6. The apparatus of claim 2 wherein said viscous composition has a viscosity of about 12,000 to 50,000 cP.

7. The apparatus of claim 6 wherein said applicator head has an average porosity of about 150 to 400 μm.

8. The apparatus of claim 2 wherein said applicator head has an average porosity of about 150 to 400 μm.

9. The apparatus of claim 1, 2, 3, 4, 5, 6, 7, or 8 wherein said transport mechanism comprises a platform situated below said applicator head within said container, the portion of said container between said platform and said applicator head defining said reservoir, said platform being adapted to move toward said applicator head.

10. The apparatus of claim 9 wherein said transport mechanism comprises a turn buckle coupled to a threaded shaft which is threadedly engaged to said platform, wherein rotation of said turn buckle causes rotation of said threaded shaft which causes said platform to move toward said applicator head.

11. The apparatus of claim/wherein said upper surface has a smooth rounded contoured shape to engage the underarm portion of a human body.

12. Apparatus for dispensing a viscous antiperspirant or deodorant composition to an under arm portion of a human body, said apparatus comprising a container which defines a reservoir that is at least partially filled with said viscous composition, and an applicator head having interconnected pores affixed at one end of said container, wherein said applicator head comprises a rigid, non-deformable, sintered porous polyolefin with an externally disposed upper surface and an internally disposed bottom surface which is in contact with said viscous composition over a major portion of said bottom surface, said apparatus further comprising a transport mechanism to force said viscous composition from said reservoir through the pores of said applicator head for distribution of said viscous composition onto said upper surface, wherein said transport mechanism comprises (i) a platform situated below said applicator head within said container, the portion of said container between said platform and said applicator head defining said reservoir, and (ii) a turn buckle coupled to a threaded shaft which is threadedly engaged to said platform, wherein rotation of said turn buckle causes rotation of said threaded shaft which causes said platform to move toward said applicator head.

13. The apparatus of claim 12 wherein said applicator head comprises a sintered porous polyethylene.

14. The apparatus of claim 13 wherein said applicator head has an average porosity of about 150 to 400 μm.

15. The apparatus of claim 12 wherein said viscous composition has a viscosity of about 12,000 to 50,000 cP.

16. The apparatus of claim 15 wherein said applicator head has an average porosity of about 150 to 400 μm.

17. The apparatus of claim 12 wherein said upper surface has a smooth rounded contoured shape to engage the underarm portion of a human body.

* * * * *